US00PP29436P3

(12) United States Plant Patent
Brazelton et al.

(10) Patent No.: US PP29,436 P3
(45) Date of Patent: Jul. 3, 2018

(54) BLUEBERRY PLANT NAMED 'FCM12-038'

(50) Latin Name: ***Vaccinium corymbosum* hybrid**
Varietal Denomination: FCM12-038

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/330,406

(22) Filed: Sep. 16, 2016

(65) Prior Publication Data

US 2017/0099757 P1 Apr. 6, 2017

Related U.S. Application Data

(60) Provisional application No. 62/284,550, filed on Oct. 2, 2015.

(51) Int. Cl.
*A01H 5/08* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
(74) *Attorney, Agent, or Firm* — Hahn Loeser & Parks, LLP—San Diego

(57) ABSTRACT

The new blueberry plant variety 'FCM12-038' is provided. The new blueberry plant originated from a cross of 'FF03-158' (female parent, unpatented) by 'FL01-06' (pollen parent, unpatented). 'FCM12-038' is a commercial variety intended for the hand harvest fresh market. The variety has medium vigor, ripens very early and produces a large berry with good firmness, and a small picking scar on fruit derived from the current season's growth. 'FCM12-038' was selected for use in an evergreen production system in areas where zero effective chilling hours may be accumulated.

8 Drawing Sheets

Latin name of the, genus, and species:
*Genus—Vaccinium.*
Species—*corymbosum* hybrid.
Variety denomination: The new blueberry plant claimed is of the variety denominated 'FCM12-038'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM12-038', as herein described and illustrated. The new blueberry plant variety 'FCM12-038' was selected near Colima, state of Colima, Mexico in 2012. 'FCM12-038' is a commercial variety intended for the hand harvest fresh market. The variety has medium vigor, ripens very early and produces a large berry with good firmness, and a small picking scar on fruit derived from the current season's growth. 'FCM12-038' was selected for use in an evergreen production system in areas where zero effective chilling hours may be accumulated. The growing region of Colima, Mexico where 'FCM12-038' was originally selected is at a low latitude (~19.5° N) with a sub-tropical climate. In this region, temperatures rarely fall below 45° F. (the maximum temperature at which blueberry buds accumulate chill units to break dormancy) and day lengths only vary from between 10.8 hours in December to 13.2 hours in June. Under these conditions, many traditional low-chill blueberry varieties (developed in latitudes 25°-35°) do not produce flower buds or flowers. In the case of blueberry varieties that do flower under these conditions, the flowers are produced primarily on current season's growth that is often referred to as a 'primocane' in the blueberry industry. The 'primocane' inflorescences tend to be very elongated in form compared to the inflorescence produced at higher latitudes from dormant buds, and the fruit often does not abscise well from the pedicel, resulting in a large picking scar which greatly limits shelf life. The blueberry industry in this area is dominated by the variety 'Biloxi' (not patented). 'Biloxi' (not patented) is one of the few traditional low chill varieties that grows well and produces fruit with a good picking scar in this growing environment. However, 'Biloxi' (not patented) often produces an excessive proportion of small, unmarketable fruit. 'FCM12-038' was exceptional because it flowered and fruited more than most genotypes but also had large, firm fruit with a small picking scar. 'FCM12-038' also flowers very quickly after pruning, resulting in earlier fruit production than 'Biloxi' (non patented).

SUMMARY OF THE INVENTION

Pedigree and History: The new blueberry plant originated from a cross of 'FF03-158' (female parent, unpatented) by 'FL01-06' (pollen parent, unpatented).

The cross that produced 'FCM12-038' (denominated by the cross code 'X08-123') was made in Lowell, Oreg., USA in 2008.

The new blueberry plant variety 'FCM12-038' was initially propagated by softwood cuttings in 2012 in Lowell, Oreg., USA. Rooted plants from these cuttings were field planted in Tala, Jalisco, Mexico and also shipped to Lowell, Oreg., USA in 2013. Additional plants have been propagated via softwood cuttings from the plants established in Tala, Mexico in 2014. The plants sent to Lowell, Oreg. were also propagated via softwood cuttings in 2014 and successfully used to establish in vitro culture lines in 2014.

The seedling family that produced 'FCM12-038' was initially grown in 50 cell propagation trays and shipped to Mexico in March, 2011, after the plants had reached sufficient size to be field planted. They were planted in a commercial blueberry field near Colima City, state of Colima, Mexico and evaluated for fruit production and quality beginning in December 2011. 'FCM12-038' was selected in 2012 because it flowered prolifically in a zero chill, evergreen production system and produced fruit with large size, firm texture, and a small picking scar. After being selected in Colima, 'FCM12-038' was propagated by softwood cuttings and a ten plant plot was established in Tala, state of Jalisco, Mexico (near Guadalajara). The ten plant plot was evaluated for fruit quality and yield in comparison to the standard varieties 'Biloxi' (not patented) and 'Ventura' (U.S. Pat. No. 24,606) beginning in December, 2013. After two harvest seasons of evaluation, the yield and fruit quality of 'FCM12-038' were deemed sufficiently good to warrant launching it as a commercial variety.

The new blueberry plant 'FCM12-038' as it grows in Tala, Mexico is distinguished by an upright growth habit, moderate vigor, widely spaced internodes, wide leaves with a rounded base, urceolate flowers, very early flowering and fruiting following pruning, and firm, large fruit with a moderately dark color and flattened shape. The new blueberry plant 'FCM12-038' consistently produces larger fruit than the standard variety 'Biloxi' (not patented), which is a very desirable characteristic.

Plants of 'FCM12-038' propagated from softwood cuttings or in vitro are phenotypically stable and exhibit the same characteristics as the original plant. The parents 'FF03-158' (not patented) and 'FL01-06' (not patented) have not been evaluated in the same environment of Mexico that 'FCM12-038' was selected in. However, in California, USA 'FF03-158' (not patented) had fruit with a texture that was softer and more mealy than fruit of 'FCM12-038' grown in Mexico. The fruit of 'FF03-158' grown in California, USA were also lighter blue in color than fruit of 'FCM12-038' grown in Mexico. Similarly, the blueberry plant 'FL01-06' grown in California, USA had a plant with shorter internodes and produced fruit that were more round in shape than fruit of 'FCM12-038'.

DETAILED BOTANICAL DESCRIPTION

Figure 1:
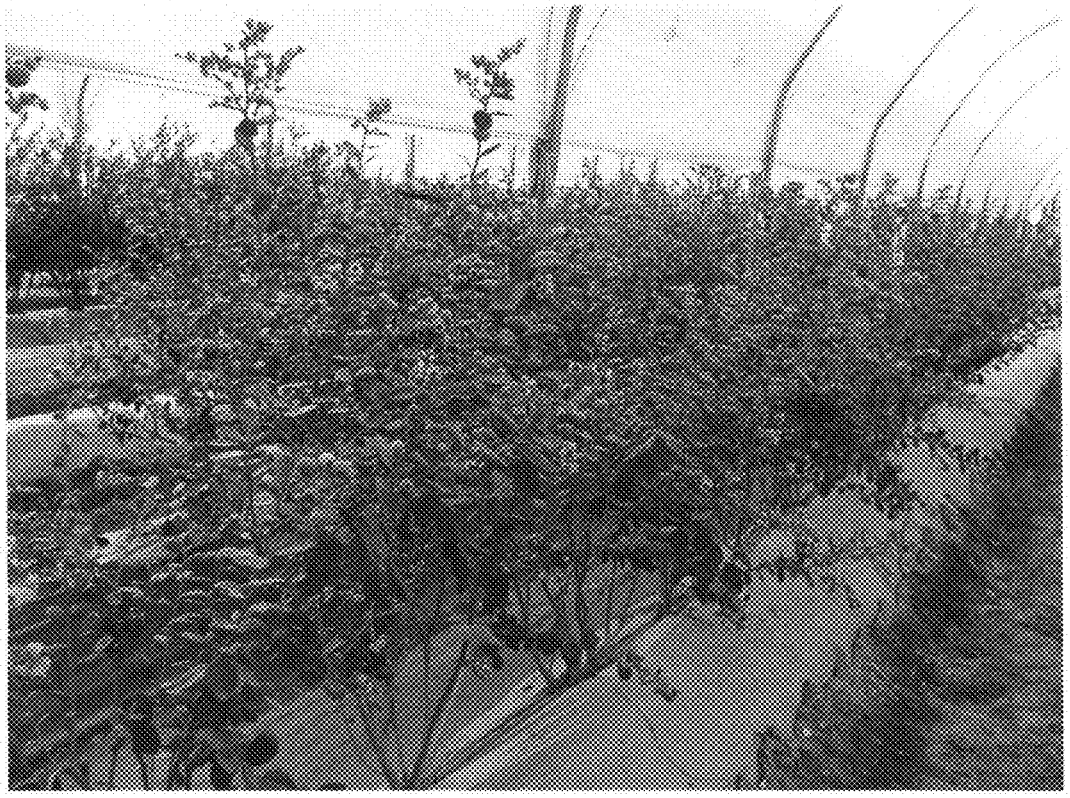
FIG. 1 is a photograph of 'FCM12-038' plant showing growth habit and fruiting in Tala, Jalisco, Mexico on Nov. 27, 2014.
Figure 2:
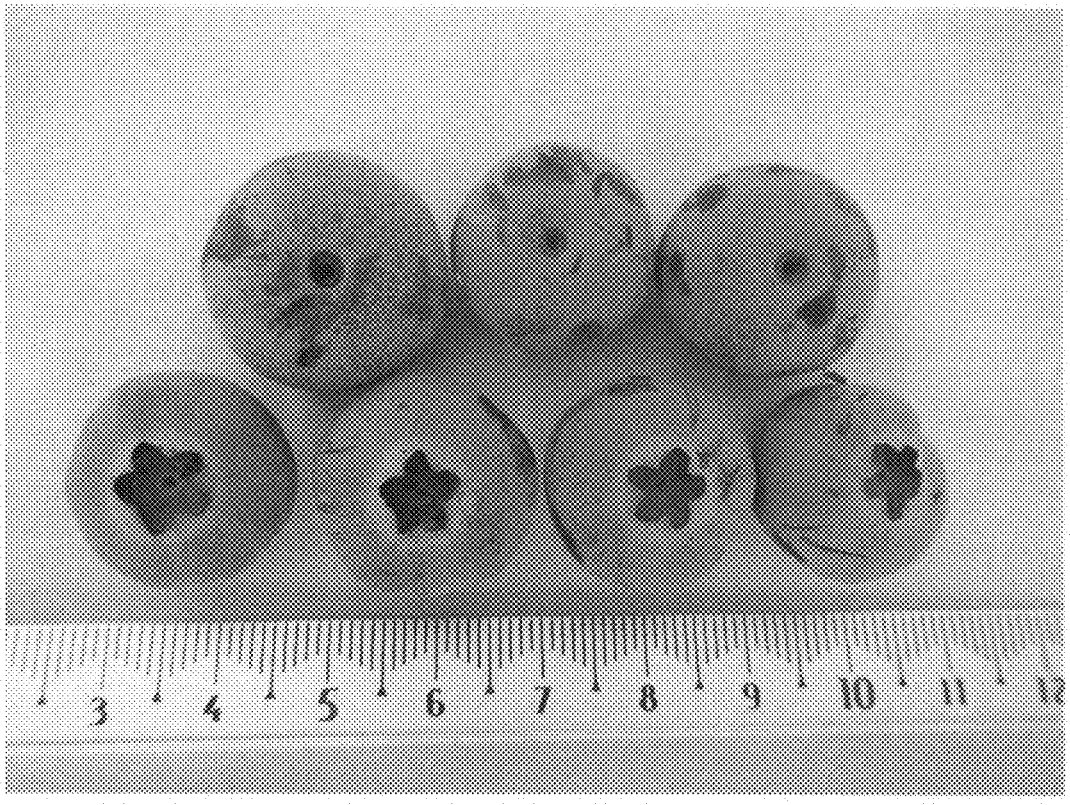
FIG. 2 is a photograph of entire fruit of 'FCM12-038' grown in Tala, Jalisco, Mexico on Feb. 26, 2015.
Figure 3:
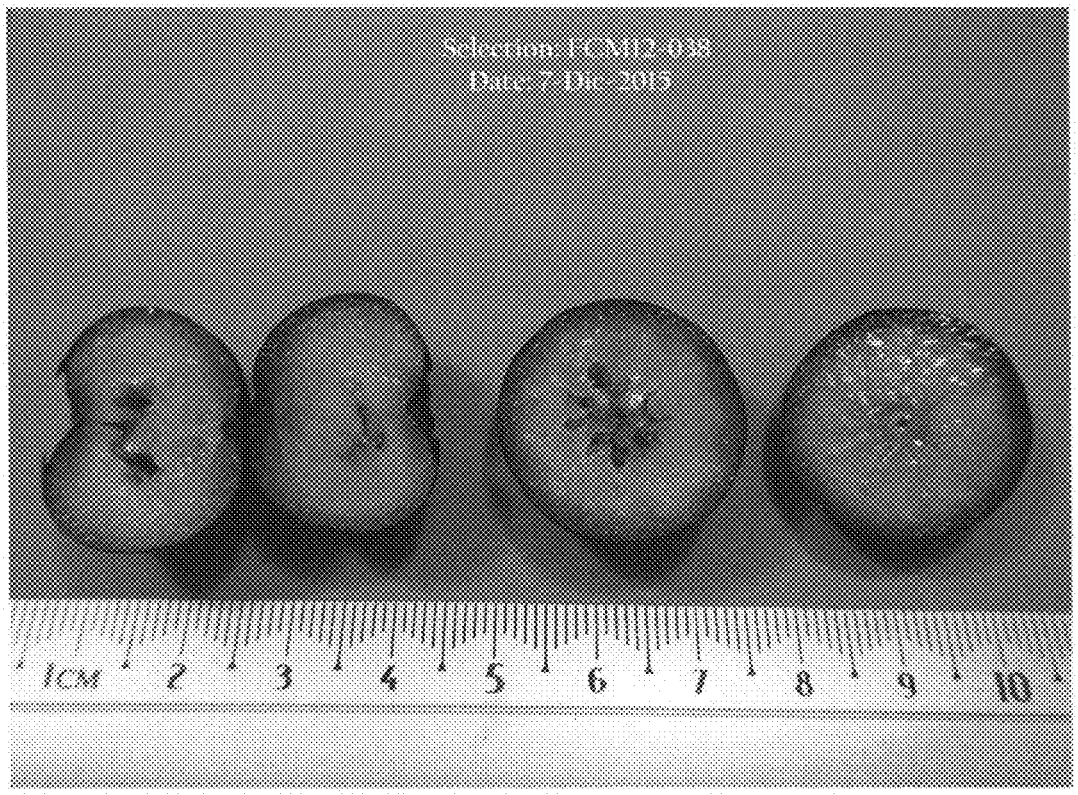
FIG. 3 is a photograph of fruit from 'FCM12-038' in vertical (left) and horizontal (right) cross section. Fruit was grown in Tala, Jalisco, Mexico and photographed on Dec. 7, 2015.
Figure 4:
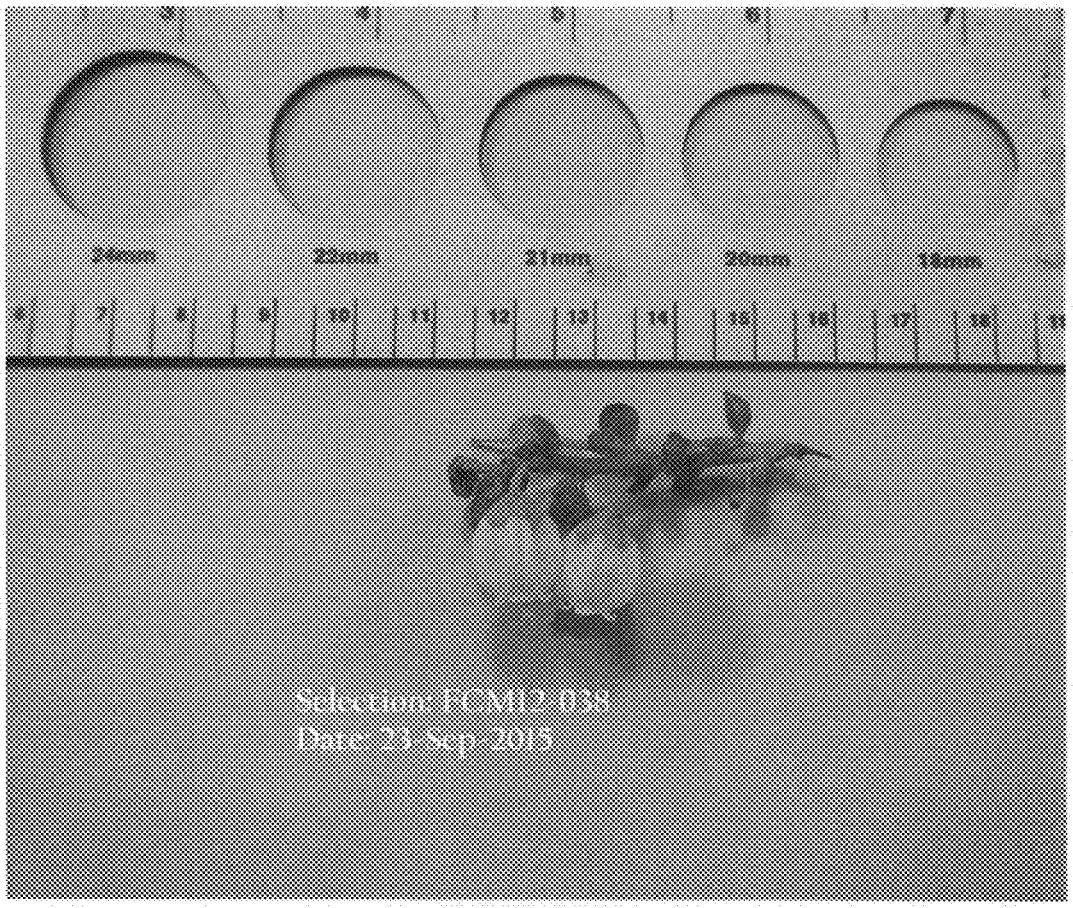
FIG. 4 is a photograph of flowers of 'FCM12-038' grown in Tala, Jalisco, Mexico and photographed on Sep. 23, 2015.
Figure 5:
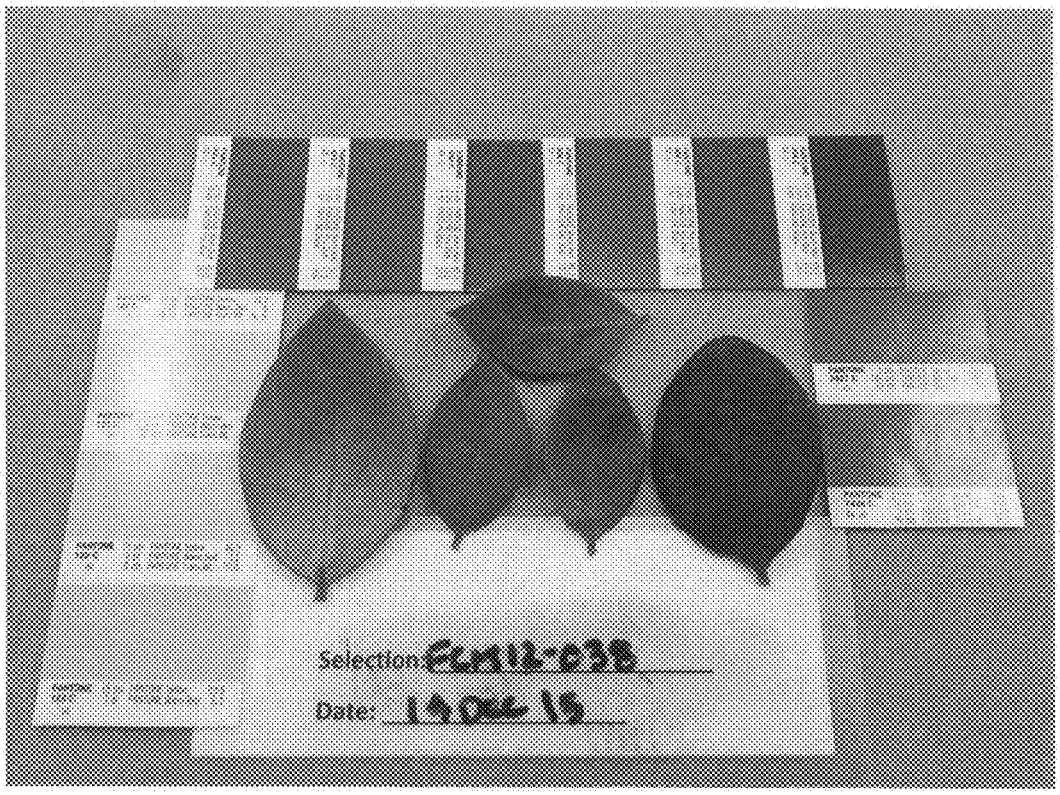
FIG. 5 is a photograph of leaves of 'FCM12-038' showing fall color from plants grown in Lowell, Oreg. and photographed on Dec. 15, 2015.
Figure 6:
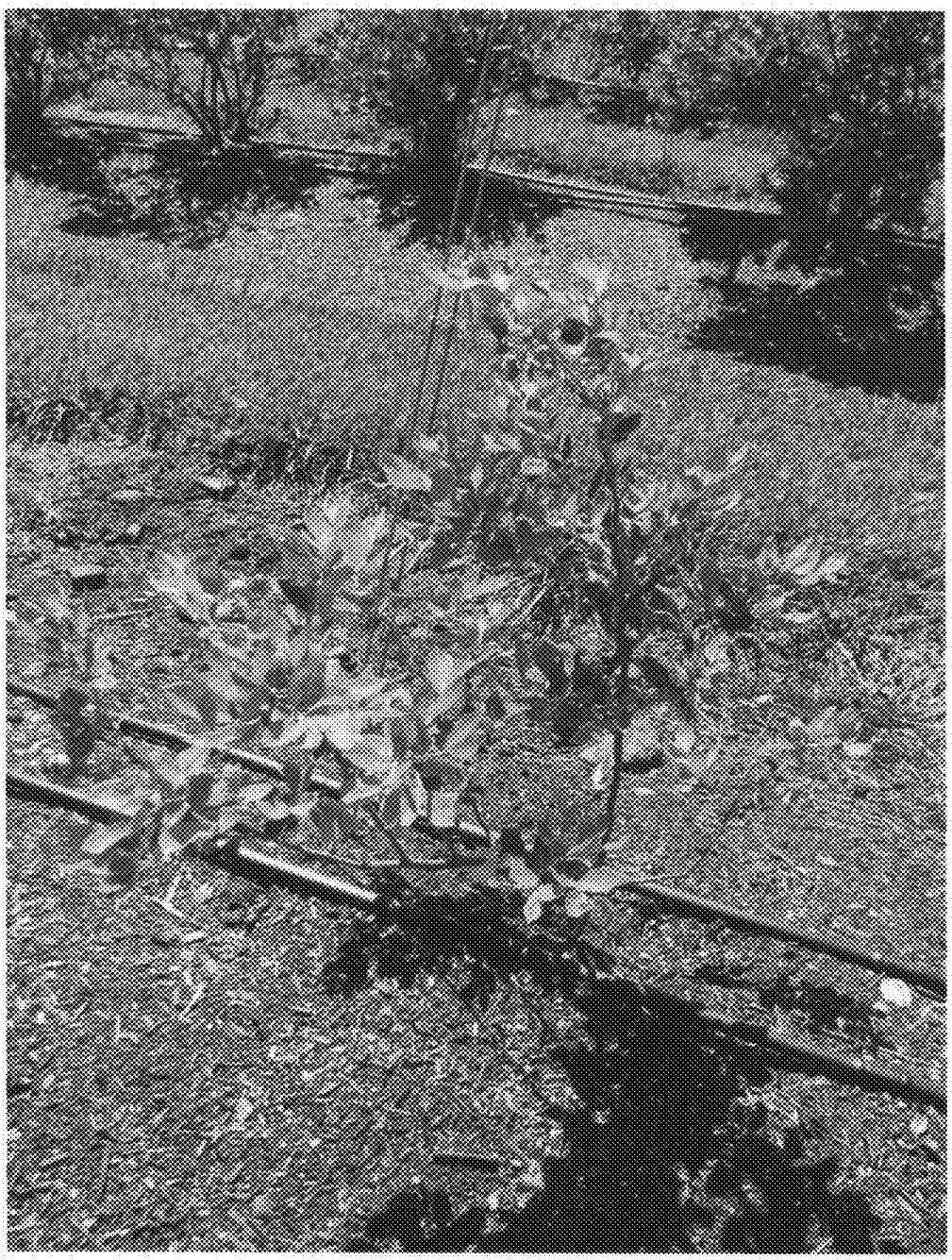
FIG. 6 is a photograph of new growth of 'FCM12-038' on plants grown in Lowell, Oreg. and photographed on Jun. 15, 2015.
Figure 7:
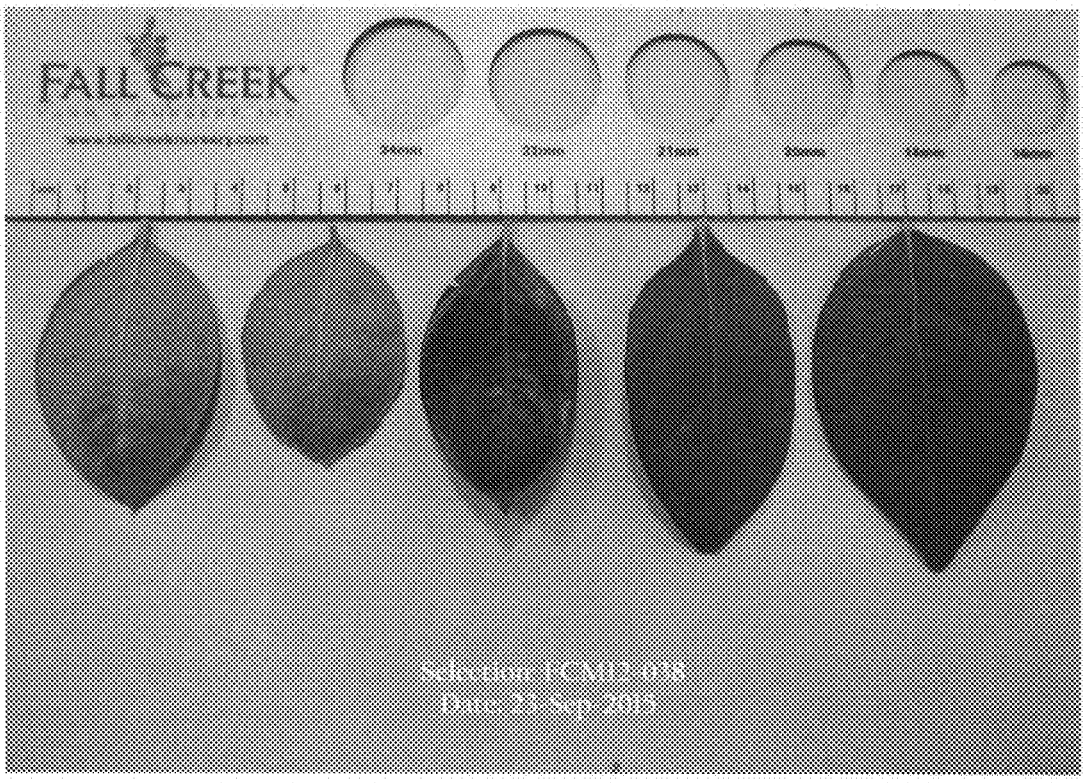
FIG. 7 is a photograph of leaves of 'FCM12-038' on plants grown in Tala, Jalisco, Mexico and photographed on Sep. 23, 2015.
Figure 8:
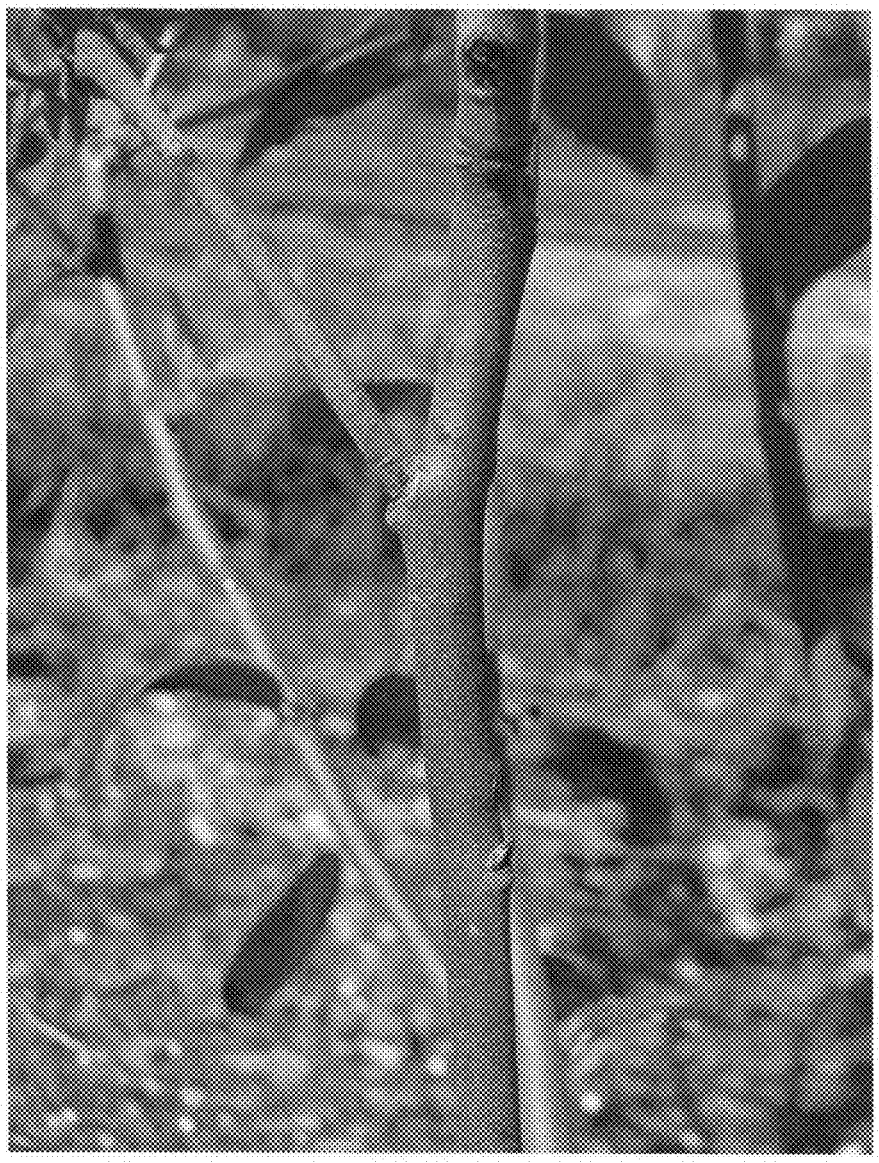
FIG. 8 is a photograph of one year canes of 'FCM12-038' showing bark color on plants grown in Lowell, Oreg. and photographed on Apr. 15, 2016.

The following detailed description sets forth the distinctive characteristics of 'FCM12-038'. The data which defines these characteristics was collected from asexual reproductions of the original selection. Dimensions, sizes, colors, and other characteristics are approximations and averages set forth as accurately as possible. All measurements are the average of five observations. The plant history was taken on mature plants approximately 2 years of age, and the descriptions relate to plants grown in the field in Tala, state of Jalisco, Mexico unless otherwise noted (observations on fall leaf color and some other traits were collected on plants grown in Lowell, Oreg.). Descriptions of fruit characteristics were made on fruit grown in Tala, State of Jalisco, Mexico. Color designations are from "The Pantone Book of Color" (by Leatrice Eiseman and Lawrence Herbery, Harry N. Abrams, Inc., Publishers, New York 1990) unless noted otherwise. Where the Pantone color designations differ from the colors in the photographs, the Pantone colors are accurate.

VARIETY

Classification:

a. *Family*.—Ericaceae.
b. *Genus*.—*Vaccinium*.
c. *Species*.—*corymbosum* hybrid.
d. *Common name*.—Southern highbush blueberry.

Parentage:

a. *Female parent*.—'FF03-158'.
b. *Male parent*.—'FL01-06'.

Market class: Commercial blueberry variety intended for the hand harvest fresh market.

PLANT

General:

a. *Parentage*.—Female parent 'FF03-158' (unpatented). Male parent 'FL01-06' (unpatented).
b. *Plant height*.—Average of 89.4 cm.
c. *Plant width*.—Average of 78.3 cm.
d. *Growth habit*.—Semi-erect.
e. *Growth*.—Vigorous.
f. *Productivity*.—Good. Average of 3.18 kilos per plant, per year on a one-year old plant in Tala, Jalisco, Mexico.
g. *Cold hardiness*.—Not determined, likely USDA zone 7 given southern highbush parentage.
h. *Chilling requirement*.—Not determined. Capable of fruiting well with zero chill when maintained in an evergreen state of growth.
i. *Leafing*.—Moderate.

j. *Twigginess*.—Low.
k. *Resistance/susceptibility to root rot* (*phytopthora cinnamomii*).—Does not appear to be overly susceptible.
l. *Resistance/susceptibility to stem blight* (*botryosphaeria sp..*).—Does not appear to be overly susceptible.
m. *Resistance/susceptibility to phomopsis twig blight* (*phomopsis vaccinii*).—Not noted.
n. *Resistance/susceptibility to botrytis* (*botrytis cinerea*).—Not noted.
o. *Resistance/susceptibility to leaf spot* (*septoria spp..*).—Not noted.
p. *Resistance/susceptibility to leaf rust* (*naohidemyces vaccinii*).—Does not appear to be overly susceptible.
q. *Resistance/susceptibility to bud mites* (*acalatus vaccinii*).—Not noted.

STEM

General:
a. *Suckering tendency*.—Low.
b. *Mature cane color*.—Pantone Russet Brown 19-1338, Peridot 17-0336, Mahogany 18-1425.
c. *Mature cane length*.—Average of 33.6 cm.
d. *Mature cane width*.—Average of 15.71 mm on a two year old plant.
e. *Bark texture*.—Rough.
f. *Fall color on new shoots*.—Not observed in Tala, Mexico. Pantone colors Maroon 18-1619, Green Oasis 15-0538 in Lowell, Oreg.
g. *Surface texture of new wood*.—Smooth.
h. *Internode length on strong, new shoots*.—Average of 18.7 mm.
i. *Average number of buds per fruiting lateral*.—Average 4.

FOLIAGE

General:
a. *Time of beginning of leaf bud burst*.—Early March in Lowell, Oreg.
b. *Leaf color* (*top side*).—Pantone Cypress 18-0322.
c. *Leaf color* (*under side*).—Pantone Water Cress 17-0220.
d. *Fall leaf color*.—Not observed in Tala, Mexico. In Lowell, Oreg.: Pantone colors Raisin 19-1606, Pompeii 18-1426, Pompeian Red 18-1426, True Red 19-1664, Aurora Red 18-1550, Snapdragon 13-0840, Barn Red 18-1531, and Peridot 17-0336.
e. *Leaf arrangement*.—Alternate.
f. *Leaf shape*.—Broadly elliptic.
g. *Leaf margins*.—Entire.
h. *Leaf venation*.—Anastomosing.
i. *Leaf apices*.—Slightly acute to obtuse.
j. *Leaf bases*.—Obtuse to rounded.
k. *Leaf length*.—Average of 49.8 mm.
l. *Leaf width*.—Average of 33.4 mm.
m. *Leaf length/width ratio*.—Average of 1.49.
n. *Leaf nectaries*.—Absent.
o. *Pubescence of upper side*.—Absent.
p. *Pubescence of lower side*.—Absent.
q. *Cross sectional profile*.—Slightly revolute.
r. *Longitudinal profile*.—Plane.
s. *Attitude*.—Acute to slightly acute.

Petioles:
a. *Length*.—Average of 3.15 mm.
b. *Width*.—Average of 1.90 mm.
c. *Color*.—Pantone Moss 16-0532.
d. *Surface texture*.—Smooth.

FLOWERS

General:
a. *Self-compatibility*.—Good, 82% of self-pollinated flowers reaching maturity.
b. *Time of beginning of flowering*.—In Tala, Mexico approximately September 25, depending on time of previous pruning. In Lowell, Oreg. flowering begins in mid to late March.
c. *Time of* 50% *anthesis*.—In Tala, Mexico approximately November 30, depending on time of previous pruning. In Lowell, Oreg. 50% anthesis occurs at approximately late March or early April.
d. *Flower shape*.—Urceolate.
e. *Flower fragrance*.—Faint, sweet, slightly floral (like lilac).
f. *Immature flower color*.—Pantone Powder pink 14-1511 and Reed Yellow 13-0915.
g. *Pollen staining*.—95% fertile, estimated by staining with 2% acetocarmine dye.
h. *Self-compatibility*.—Good, 82% of self-pollinated flowers reaching maturity.

Corolla:
a. *Color*.—Pantone Antique white 11-0105.
b. *Length*.—Average of 10.43 mm.
c. *Width*.—Average of 9.754 mm.
d. *Aperture width*.—Average of 4.48 mm.
e. *Anthocyanin coloration of corolla at time of anthesis*.—Low.
f. *Corolla ridges*.—Present, distinct.
g. *Protrusion of stigma*.—Recessed: average of –0.2 mm below lip of corolla.

Inflorescence:
a. *Length*.—Average of 42.3 mm.
b. *Diameter*.—Average of 34.5 mm.
c. *Length of peduncle*.—Average of 31.6 mm.
d. *Surface texture of peduncle*.—Rough.
e. *Color of peduncle*.—Pantone Leaf green 15-0332, Cranberry 17-1545.
f. *Length of pedicel*.—Average 5.17 mm.
g. *Surface texture of pedicel*.—Smooth.
h. *Color of pedicle*.—Pantone Spinach green 16-0439 and Barn Red 18-1531.
i. *Number of flowers per cluster*.—8.2.
j. *Flower cluster density*.—Low.

Calyx (with sepals):
a. *Diameter*.—Average of 6.72 mm.
b. *Color* (*sepals*).—Pantone Lettuce Green 13-0324.
c. *Calyx surface*.—Smooth.

Stamen:
a. *Length*.—Average of 7.6 mm.
b. *Number per flower*.—Average of 10.4.
c. *Filament color*.—Pantone Mellowgreen 12-0426.

Pistil:
a. *Length*.—Average of 9.64 mm.
b. *Ovary color* (*exterior*).—Pantone Spinach green 16-0439.
c. *Style*.—Length — Average of 9.35 mm.

Anther:

a. *Length*.—Average of 2.03 mm.
b. *Number*.—10.
c. *Color*.—Pantone Burnt Orange 16-1448.

Pollen:

a. *Abundance*.—Very abundant.
b. *Color*.—Pantone Antique White 11-0105.

FRUIT

General:

a. *Time of fruit ripening*.—In Tala, Mexico approximately November 30, depending on timing of previous pruning. In Lowell, Oreg., approximately June 20.
b. *Fruit development period*.—Approximately 60 days.
c. *Mean harvest date*.—In Tala, Mexico peak harvest occurs on approximately November 30, depending on timing of previous pruning.
d. *Mean date last pick*.—In Tala, Mexico the last pick occurs on approximately May 1$^{st}$, depending on timing of previous pruning.
e. *Cluster density*.—Medium.
f. *Berry cluster*.—Medium.
g. *Berries per cluster*.—Average of 6.6.
h. *Unripe fruit color*.—Pantone Reed 13-0215.
i. *Ripe berry color*.—Pantone Gull 17-3802.
j. *Berry skin color after polishing*.—Pantone Dark navy 19-4014.
k. *Berry surface wax abundance*.—medium.
l. *Berry flesh color*.—Pantone Beechnut 14-0425.
m. *Berry weight*.—Average 2.2 grams.
n. *Berry height from calyx to scar*.—Average 13.67 mm.
o. *Berry diameter*.—Average of 20.23 mm.
p. *Calyx aperture*.—Average of 6.98 mm.
q. *Calyx depth*.—Average of 1.8 mm.
r. *Pedicel length*.—Average of 9.06 mm.
s. *Pedicel surface texture*.—Smooth.
t. *Berry detachment force*.—Moderate to slightly difficult.
u. *Berry shape*.—Oblong.
v. *Fruit stem scar*.—Small.
w. *Berry flavor*.—Generally sweet, flavor not strong or distinct.
x. *Sweetness when ripe*.—High.
y. *Firmness when ripe*.—Good to excellent. (1) Acidity when ripe — Low. (2) Storage quality — Excellent. (3) Suitability for mechanical harvesting — Low. (4) Self-fruitfulness — Good. (5) Uses — Commercial fruit production for the fresh market.

SEED

General:

a. *Seed abundance in fruit*.—Low.
b. *Seed color*.—Pantone Cork 16-1422.
c. *Seed dry weight*.—Average of 8 mg/seed (100 seeds).
d. *Seed length*.—Average of 2.44 mm.

COMPARISON BETWEEN PARENTAL AND COMMERCIAL CULTIVARS

TABLE 1

Comparison Table.

| Denomination of similar variety | Characteristic for comparison | State of expression of similar variety | State of expression of candidate variety (FCM12-038) |
|---|---|---|---|
| FF03-158 (not patented) | Fruit firmness | Low. Soft with mealy texture. | Firm, berry flesh is solid. |
| FF03-158 (not patented) | Growth habit | Spreading | Semi-erect |
| FL01-06 (not patented) | Fruit shape | Round | Oblate |
| FL01-06 (not patented) | Leaf apex shape | Acute to acuminate | Acute to obtuse |
| Biloxi (not patented) | Leaf margin | Slightly serrate | Entire |
| Biloxi (not patented) | Fruit size | Average 2.2 grams | Average 1.16 grams |
| Ventura (U.S. Plant Pat. No. 24,606) | Flower shape | Cylindrical | Urceolate |

The invention claimed is:

1. A new and distinct variety of blueberry plant named 'FCM12-038' substantially as illustrated and described herein.

* * * * *